(12) United States Patent
Christmann et al.

(10) Patent No.: US 7,049,480 B1
(45) Date of Patent: May 23, 2006

(54) METHODS OF ENUCLEATING AN AVIAN OOCYTE OR ZYGOTE USING TWO-PHOTON LASER SCANNING MICROSCOPY

(75) Inventors: Leandro Christmann, Watkinsville, GA (US); Scott L. Pratt, Athens, GA (US); Jeffrey C. Rapp, Athens, GA (US)

(73) Assignee: AviGenics, Inc., Athens, GA (US)

( * ) Notice: Subject to any disclaimer, the term of this patent is extended or adjusted under 35 U.S.C. 154(b) by 0 days.

(21) Appl. No.: 09/654,293

(22) Filed: Sep. 1, 2000

(51) Int. Cl.
*C12N 15/00* (2006.01)
*C12N 5/00* (2006.01)
*C12N 5/02* (2006.01)
*C12N 5/06* (2006.01)
*C12N 5/10* (2006.01)

(52) U.S. Cl. .................... 800/24; 435/325; 435/349

(58) Field of Classification Search ............... 800/3, 800/18, 21, 22, 25, 24; 435/455, 463, 320.1, 435/325, 349
See application file for complete search history.

(56) References Cited

U.S. PATENT DOCUMENTS

| | | | |
|---|---|---|---|
| 4,903,635 A | 2/1990 | Hebrank | 119/1 |
| 4,997,763 A | 3/1991 | Hughes et al. | 435/172.3 |
| 5,011,780 A | 4/1991 | Perry | 435/317.1 |
| 5,106,617 A | 4/1992 | Federicksen et al. | 424/85.2 |
| H1065 H | 6/1992 | Salter et al. | 800/2 |
| 5,158,038 A | 10/1992 | Sheeks et al. | 119/6.8 |
| 5,162,215 A | 11/1992 | Bosselman et al. | 435/172.3 |
| 5,258,307 A | 11/1993 | Simkiss et al. | 435/317.1 |
| 5,285,750 A | 2/1994 | Molian et al. | 119/174 |
| 5,340,740 A | 8/1994 | Petitte et al. | 435/240.2 |
| 5,656,479 A | 8/1997 | Petitte et al. | 435/349 |
| 5,699,751 A | 12/1997 | Phelps et al. | 119/6.8 |
| 5,784,992 A | 7/1998 | Petitte et al. | 119/6.8 |
| 5,897,998 A | 4/1999 | Speksnijder et al. | 435/349 |
| 6,020,465 A | 2/2000 | Sekellick et al. | 530/351 |
| 6,027,722 A | 2/2000 | Hodgson | 424/93.21 |

FOREIGN PATENT DOCUMENTS

| | | |
|---|---|---|
| EP | GB 2331751 A | 6/1999 |
| EP | GB 2331751 B | 1/2000 |
| WO | WO 90/11355 | 10/1990 |
| WO | WO 97/07668 * | 3/1997 |
| WO | WO 97/47739 | 12/1997 |
| WO | WO 98/14053 | 4/1998 |
| WO | WO 98/38283 | 9/1998 |
| WO | WO 99/10505 | 3/1999 |
| WO | WO 99/19472 | 4/1999 |
| WO | WO 00/09674 | 2/2000 |
| WO | WO 00/11151 A2 | 3/2000 |

OTHER PUBLICATIONS

Westhusin et.al.; Cloning to Reproduce Desired Genotypes, 2000, Theriogenology 55: 35-49.*
Fehilly et.al.; Interspecific chimaerism between sheep and goat, 1983, Nature vol. 307: 634-636.*
Kato et.al.; Nuclear Transplantation of Mouse Fetal Germ Cells, 1992, Theriogenology 37: 769-778.*
Wall; Transgenic Livestock: Progress and Prospects for the Future, 1996, Theriogenology 45: 57-68.*
Dinnyes et.al.; Somatic Cell Nuclear Transfer: Recent Progress and Challenges, 2001, Cloning and Stem Cells, vol. 4: 81-90.*
Chang et.al.; Production of Germline Chimeric Chickens by Transfer of Cultured Primiordial Germ Cells, 1997, Cell Biology International, vol. 21: 495-499.*
Campbell. J. of Anat., 200:26-275 (2002).*
Pennisi and Vogel. Science, 288:1722-1727.*
König et al. Nature, 377:20-21 (Sep. 5, 1995).*
König et al. Human Reprod., 11(10):2162-2164 (1996).*
Askew et al. "Site-Directed Point Mutations in Embryonic Stem Cells: a Gene-Targeting Tag-and-Exchange Strategy" Molecular and Cellular Biology 13(7):4115-4124 (Jul. 1993).
Bosselman et al. "Germline Transmission of Exogenous Genes in the Chicken" Science 243:533-535 (Jan. 27, 1989).
Cibelli et al. "Cloned Transgenic Calves Produced from Nonquiescent Fetal Fibroblasts" Science 280:1256-1258 (May 22, 1998).
Eyestone et al. "Nuclear transfer from somatic cells: applications in farm animal species" J. Reprod. Fertil. Supplement 54:489-497 (1999).
Gilbert et al. "A Technique for the Fistulation of the Hen's Oviduct Through the Abdominal Wall, with Recovery of the Ovum" J. Reprod. Fertil. 5:451-453 (1963).
Harvey "Nuclear transfer and gene targeting in domestic animals: bioreactors of the future" Advanced transgenesis and cloning:genetic manipulation in animals, Electronic Workshop Presentation:Paper No. 8 (Sep. 15, 1998).
Hasty et al. "Introduction of a subtle mutation into the Hox-2.6 locus in embryonic stem cells" Nature 350:243-246 (Mar. 21, 1991).
Leff "Cloning method does dolly one better" BioWorld Today 11(159):1,4-7 (Aug. 17, 2000).
Le Mouellic et al. "Targeted replacement of the homeobox gene Hox-3.1 by the *Escherichia coli* lacZ in mouse chimeric embryos" Proc. Natl. Acad. Sci. USA 87:4712-4716 (Jun. 1990).
Love et al. "Transgenic birds by DNA microinjection" Bio/Technology 12(1):60-3 (Jan. 1994).

(Continued)

*Primary Examiner*—Anne-Marie Falk
*Assistant Examiner*—Thaian N. Ton
(74) *Attorney, Agent, or Firm*—Kyle D. Yesland

(57) ABSTRACT

The invention includes methods of enucleating avian eggs comprising visualizing internal structure of an avian egg utilizing TPLSM and ablating the nucleus of the egg by near-infrared light.

33 Claims, No Drawings

OTHER PUBLICATIONS

McCreath et al. "Production of gene-targeted sheep by nuclear transfer from cultured somatic cells" Nature 405:1066-1069 (Jul. 29, 2000).

McKeen "Cloning and nuclear transfer: a short glossary" Roslin Institute Online (1999).

Naito et al. "Introduction of Exogenous DNA Into Somatic and Germ Cells of Chickens by Microinjection Into the Germinal Disc of Fertilized Ova" Molecular Reproduction and Development 37:167-171 (1994).

Ochiai et al. "Synthesis of Human Erythropoietin In Vivo in the Oviduct of Laying Hens by Localized In Vivo Gene Transfer Using Electroporation" Poultry Science 77:299-302 (1998).

Olsen et al. "The site of fertilization in the domestic fowl" J. Ex. Zoology 109:355-366 (1948).

Otten et al. "The MMTV LTR Promoter is Induced by Progesterone and Dihydrotestosterone but not by Estrogen" Molecular Endocrinology 2(2):143-147 (1988).

Pancer et al. "Recovery of Ova and Their Re-Insertion Into the Hen's Oviduct Through a Fistula" British Poultry Science 30:953-957 (1989).

Piston "Imaging living cells and tissues by two-photon excitation microscopy" Trends in Cell Biology 9:66-69 (Feb. 1999).

Polejaeva et al. "Cloned pigs produced by nuclear transfer from adult somatic cells" Nature 407:505-509 (Aug. 17, 2000).

Polejaeva et al. "New Advances in Somatic Cell Nuclear Transfer: Application in Transgenesis"; Theriogenology 53:117-126 (2000).

Sanders et al. "Chicken Egg White Genes: Multihormonal Regulation in a Primary Cell Culture System" Endocrinology 116(1):398-405 (1985).

Sanders et al. Biochemistry 27:6550-6557 (1988).

Sang et al. "Episomal Replication of Cloned DNA Injected Into the Fertilised Ovum of the Hen, *Gallus domesticus*" Molecular Reproduction and Development 1:98-106 (Oct. 3, 1989).

Sang "Transgenic chickens—methods and potential applications" Tibtech 12:415-419 (Oct. 1994).

Schweers et al. "A Protein with a Binding Specificity Similar to NF-κB Binds to a Steroid-dependent Regulatory Element in the Ovalbumin Gene" Journal of Biological Chemistry 266(16):10490-10497 (Jun. 5, 1991).

Schweers et al. "The Steroid-dependent Regulatory Element in the Ovalbumin Gene Does Not Function as a Typical Steroid Response Element" Journal of Biological Chemistry 265(13):7590-7595 (May 5, 1990).

Shuman "Production of transgenic birds" Experientia 47:897-905 (1991).

Simkiss "Transgenic birds" Cambridge University Press 106-137 (1994).

Squirrell et al. "Long-term two-photon fluorescence imaging of mammalian embryos without compromising viability" Nature Biotechnology 17:763-767 (Aug. 1999).

Stacey et al. "Use of Double-Replacement Gene Targeting to Replace the Murine α-Lactalbumin Gene with Its Human Counterpart in Embryonic Stem Cells and Mice" Molecular and Cellular Biology 14(2):1009-1016 (Feb. 1994).

Tanaka et al. "Chick production by in vitro fertilization of the fowl ovum" Journal of Reproduction and Fertility 100:447-449 (1994).

Valancius et al. "Testing an 'In-Out' Targeting Procedure for Making Subtle Genomic Modifications in Mouse Embryonic Stem Cells" Molecular and Cellular Biology 11(3):1402-1408 (Mar. 1991).

Wentworth "Fistulation of the Hen's Oviduct" Poultry Science 39:782-784 (1960).

Wilmut et al. "Embryonic and somatic cell cloning" Reprod. Fertil. Dev. 10:639-643 (1998).

Wong "DNA-Treated sperm as a gene transfer vector—revisited" Department of Animal and Poultry Sciences, Virginia Tech Jul. 1996.

Yom et al. "Genetic engineering of milk composition: modification of milk components in lactating transgenic animals" American Journal of Clinical Nutrition 58 (Supplement), 299S-306S, 1993.

Dominko et al., "Dynamic imaging of the metaphase II spindle and maternal chromosomes in bovine oocytes: Implications for enucleation efficiency verification, avoidance of parthenogenesis, and successful embryonogenesis" Biology of Reproduction (Jan. 2000) vol. 62, pp. 150-154.

Fujihara et al., "Possible application of animal reproductive researches to the restoration of endangered and/or extinct wild animals—Review-" Asian-Australisian Journal of Animal Sciences (Jul. 2000) vol. 13, No. 7, pp. 1026-1034.

Morrow, "Antibody-Production Technologies, With No Single Superior Approach, Companies Must Weigh Their Own Needs" Genetic Engineering News 20(7):1, 24-25, 54-55 (Apr. 1, 2000).

* cited by examiner

US 7,049,480 B1

METHODS OF ENUCLEATING AN AVIAN OOCYTE OR ZYGOTE USING TWO-PHOTON LASER SCANNING MICROSCOPY

BACKGROUND OF THE INVENTION a) Field of the Invention

This invention relates generally to cloned cells, embryos and animals, and to methods of producing them via nuclear transfer and combinations of nuclear transfer and ovum transfer. In particular, this invention relates to the cloning of avians.

b) Description of Related Art

A major aim of biotechnologists is to produce offspring from cell populations that can be maintained in culture and to obtain stable desirable phenotypes that transmit the required traits through the germ line. For nuclear transfer, the availability of cultured cell lines facilitates cell cycle synchronization of the donor nucleus and allows optimization of cell cycle co-ordination in the reconstituted embryo. In order to obtain stable desirable phenotypes, nuclear transfer from cultured cell populations provides a promising alternative route to genetic modification. Until recently, genetic modification in farm animals was limited to pronuclear injection wherein the required gene is injected into the pronucleus of a zygote. Although pronuclear injection has been applied in several species including mice, rabbits, pigs, sheep, goats and cattle, there are a number of disadvantages with this technique. Integration of the gene does not always occur during the first cell cycle, resulting in the production of mosaic embryos. In addition, integration occurs at random within the genome, resulting in variable expression of the gene product. Thus, the production of an animal having the required phenotype capable of germ line transmission may require the generation of several transgenic lines, as well as extensive breeding of founder animals. In comparison, the production of animals by nuclear transfer from cells that can be maintained in culture offers a number of advantages over pronuclear injection. In nuclear transfer, the cells to be used as nuclear donor cells may be sexed, optionally genetically modified, and selected in culture before their use. The resultant animal is produced from a single nucleus and mosaics can therefore be avoided. The genetic modification is easily transmitted to the offspring. In addition, all the cells in the animal are likely to contain the transgene and expression can be obtained in the tissues of interest.

The ability to produce live offspring by nuclear transfer from cultured somatic cells also provides a route for the precise genetic manipulation of animal species. Such modifications include the addition or "knock-in" of genes, and the removal or inactivation or "knock-out" of genes or their control sequences (Polejaeva et al., Theriogenology, 53(1): 117–26, 2000). Gene targeting techniques also promise the generation of transgenic animals in which specific genes coding for endogenous proteins have been replaced by human genes coding for exogenous human proteins. In 1993, Yom and Bremmel suggested that genes coding for major proteins in cow's milk could be replaced by human counterparts. Cows modified in this fashion would produce milk containing human milk proteins, which may be more nutritious for human infants and more suitable for infant formula manufacture (Yom, H. C. and Bremmel, R. D., American Journal of Clinical Nutrition, 1993, 58 (Supplement) 306S). Methods for producing exogenous proteins in the milk of pigs, sheep, goats and cows have been reported.

Wilmut and Campbell (GB 2 331 751 B) have reported the production of reconstituted animal embryos by transferring the nucleus of a diploid donor cell into a suitable recipient cell. The donor cells are quiescent, i.e. not actively proliferating, and are characterized as being in the G0 or G1 phase. The recipient cells include oocytes at metaphase I or II, zygotes, and two-cell embryos, preferably enucleate. Enucleation is accomplished by splitting, aspiration, or irradiation. In those mechanical techniques predicated upon visualization of the nucleus, the use of a DNA-specific fluorochrome is required.

Nuclear transfer (NT) involves the transfer of the complete diploid genetic material (the DNA contained in a nucleus) from a donor cell into an enucleated recipient cell, such as a fertilized (zygote) or unfertilized (oocyte) cell. The technique involves several steps. The donor cells are first grown under special conditions in culture, increasing the number of cells by several orders of magnitude. The nuclei of the donor cells are then transferred to oocytes or zygotes, resulting in a reconstructed embryo. Activation (initiation of development) is usually artificially, most often chemically, induced. The embryos are then transplanted into female animals and allowed to develop to term. In some species (mice, cattle and sheep) the reconstructed embryos may be grown in culture until the blastocyst stage before transfer to a recipient.

The reconstruction of mammalian embryos by transfer of a blastomere nucleus to an enucleated oocyte or zygote has been reported to produce genetically identical individuals (Eyestone et al., *J. Reprod. Fertil. Suppl,*. 1999, 54:489–97). Although the number of offspring that can be produced from a single embryo is limited both by the number of blastomeres (embryos at the 32–64 cell stage are the most widely used in farm animal species) and the efficiency of the nuclear transfer procedure, the ability to produce live offspring by nuclear transfer from cells that can be propagated and maintained in culture offers many advantages. This includes the production of identical offspring over an extended period (since cultured cells can be frozen and stored indefinitely) and the ability to genetically modify and to select populations of cells of specific genotypes or phenotypes before embryo reconstruction. This objective has been achieved with the production of lambs using nuclei from cultured cells established from embryonic, fetal and adult material.

Two types of recipient cells are commonly used for nuclear transfer: oocytes arrested at the metaphase of the second meiotic division (MII) and pronuclear zygotes. In mice, enucleated, two-cell stage blastomeres have been used as recipients. In farm species, development does not always occur when pronuclear zygotes are used, except when pronuclei are exchanged between zygotes, therefore, MII-arrested oocytes have often been the recipient of choice. Oocytes arrested at MII do not contain a nucleus but a metaphase plate, where the chromosomes are arranged on the meiotic spindle. The MII chromosomes or metaphase plate are not easily visible under the light microscope in mammalian oocytes. However, visualization of the MII chromosomes or metaphase plate has been achieved with UV light using DAPI (4',6'-diamidino-2-phenylindole, hydrochloride) or Hoescht 33342 (bis-benzimide) staining. After enucleation and introduction of the donor genetic material, the reconstructed embryo must be cultured to a stage at which it can be transferred to a recipient animal, generally the morula or blastocyte stage. This can be done in vitro or in vivo (Eyestone et al., supra). Double nuclear transfer has also been reported, in which an activated, previously transferred nucleus is removed from the host unfertilized egg and transferred a second time into an enucleated fertilized embryo. (Polejaeva et al., *Nature*, 407: 505-9, 2000).

Although gene targeting techniques in combination with nuclear transfer hold tremendous promise with respect to nutritional and medical applications, current approaches suffer from several limitations, including long generation times between founder and production transgenic herds, and extensive husbandry and veterinary costs. It is therefore desirable to employ a system where the use of cultured somatic cells for nuclear transfer is more efficiently employed. One system that holds great potential is the avian reproductive system.

The avian reproductive system, including that of the chicken, is well described. The production of an egg begins with formation of the large yolk in the ovary of the hen. The unfertilized oocyte or ovum is positioned on top of the yolk sac. Upon ovulation or release of the yolk from the ovary, it passes into the infundibulum of the oviduct where it is fertilized if sperm are present. It then moves into the magnum of the oviduct which is lined with tubular gland cells. These cells secrete the egg-white proteins, including ovalbumin, lysozyme, ovomucoid, conalbumin and ovomucin, into the lumen of the magnum from which they are deposited onto the avian embryo and yolk.

Attempts at nuclear transfer in avians have remained difficult to realize. One significant challenge is the inaccessibility of the early avian egg. It is well known in the art that all forms of genetic manipulation that require visualization of the avian early embryo have been hindered by the inability to properly visualize the target structures. In nuclear transfer, after enucleation, the genetic material from the donor cell (nuclear donor) must be introduced into the enucleated oocyte. In order to produce an enucleated recipient cytoplast, it is essential to visualize the metaphase II plate or pronuclei that reside about 25 µm beneath the egg's vitelline membrane within the germinal disk. Yet, the large size and optical density of the yolk have made visualization of the avian early embryo and its structures difficult to achieve.

The hen oviduct offers outstanding potential as a protein bioreactor because of high levels of protein production, proper folding and post-translation modification of the target protein, and ease of product recovery. As a result, efforts have been made to create transgenic chickens expressing exogenous proteins in the oviduct by means of microinjection of DNA (PCT Publication WO 97/47739). Bosselman et al. describe a method for introducing a replication-defective retroviral vector into a pluripotent stem cell of an unincubated chick embryo, and further describe chimeric chickens, whose cells express an exogenous vector nucleic acid sequence. However, the percentage of G1 transgenic offspring (progeny from vector-positive male G0 birds) was low and varied between 1% and approximately 8% (U.S. Pat. No. 5,162,215). Generally, DNA injection into avian eggs has so far lead to poor and unstable transgene integration (Sang and Perry, *Mol. Reprod. Dev.*, 1:98–106, 1989, and Naito, et al., *Mol. Reprod. Dev.* 37:167–71, 1994). In addition, the use of viral vectors poses a number of limitations, including limited transgene size and potential viral infection of the offspring. The production of transgenic chickens by means of DNA microinjection (supra) is both inefficient and time-consuming. In fact, a key limitation of using any animal as a bioreactor is the time required (approximately 10 months for chickens, 2–3 years for ungulates) to introduce the desired transgene into the animal's genome.

The hen also offers a unique system for efficient direct transgenesis of the magnum gland, but initial attempts have yielded poor results. Plasmid DNAs carrying transgenes have been introduced directly into the magnum of mature hens by electroporation (Ochiai et al., *Poultry Science*, 77:299–302, 1998). Due to the large size of the oviduct of mature hens, the transient persistence of the plasmid DNAs in the cells, and the inefficiency of organ electroporation, only very low levels of protein were detected in the oviduct tissue of sacrificed hens and no expressed protein was reported as being detected in the egg. Other attempts have involved the transfection of magnum cells with expression cassettes after excision of the cells from the bird and preparation of an oviduct cell culture (Sanders et al., *Endocrinology*, 116:398–405, 1985; Sanders et al., *Biochemistry*, 27:6550–6557, 1988; Schweers et al., *Journal of Biological Chemistry*, 265:7590–7595, 1990; Otten et al., *Molecular Endocrinology*, 2:143–147, 1988; Schweers et al., *Journal of Biological Chemistry*, 266:10490–10497, 1991).

Ovum transfer, the transfer of a donor ovum to the oviduct of a recipient hen, provides another means for genetic manipulation in avians. Tanaka et al. produced chicks by in vitro fertilization (IVF) by returning the fertilized ovum into the oviduct of a recipient hen to complete the egg and shell formation. This experimental approach suggests a useful model for production of transgenic avians (Tanaka et al., *Journal of Reproduction and Fertility*, 100:447–449, 1994).

Another major challenge is the culture of the reconstructed egg. It is essential to hatch the reconstructed zygote following micromanipulation. One solution was proposed by Perry et al. (U.S. Pat. No. 5,011,780). Perry et al. use ex ovo culture to remove an embryo and yolk from a donor hen and incubate the embryo and yolk in a series of separate culture systems until hatch. Yet, this procedure is laborious and inefficient with low numbers of "test tube chickens" hatching.

It is an object of this invention to provide an improved method for visualization of the nuclear structures in a recipient cell to facilitate the process of enucleation and subsequent nuclear transfer.

It is also an object of this invention to provide an improved method for ablation of the nucleus in a recipient cell to facilitate subsequent nuclear transfer.

It is a particular object of the instant invention to provide methods that overcome the technical hurdles relating to the cloning of avians, such as inaccessibility of the avian egg and difficulty of culturing the reconstructed zygote. A new and useful method for successful nuclear transfer in avians in order to produce cloned birds would satisfy a present need in the art. Avians cloned in this manner may be genetically modified. The resulting expression and deposition of exogenous proteins in eggs, suitable for commercial use, would provide immediate benefits to the public.

SUMMARY OF THE INVENTION

The present invention provides cloned cells, cell lines, embryos, and animals and methods for their production by nuclear transfer, employing two-photon visualization, ablation or both. In one embodiment, nuclear transfer in conjunction with ovum transfer is employed. Cloned and transgenic avians, including knock-outs and knock-ins, are also provided.

In a preferred embodiment of the invention, two-photon laser scanning microscopy (TPLSM) is used to visualize nuclear structures in a recipient cell. Following visualization, the cell is enucleated, optionally with two-photon laser-mediated ablation, to provide a recipient cytoplast. Alternatively, the recipient cell may also be enucleated via cell splitting, aspiration of its nuclear structure(s), irradiation, or other enucleating procedure. Preferably, the recipient cell is removed from an animal, the nucleus visualized and ablated via two-photon laser-mediated ablation. The donor nucleus is then inserted into the recipient cell by cell fusion, microinjection, or other renucleation procedure. The replacement of the recipient cell's nucleus with the donor cell's nucleus yields a reconstructed zygote. The reconstructed zygote may be activated and allowed to develop to term in vivo or in vitro. In a preferred embodiment of the invention, the animal is an avian including, but not limited to, chickens, ducks, turkeys, quails, pheasants and ostriches.

Another aspect of the present invention provides a method of producing a cloned animal comprising nuclear transfer in combination with ovum transfer. TPLSM and two-photon laser-mediated ablation is used to perform nuclear transfer wherein the donor nucleus may be of normal karyotype or genetically modified. Accordingly, the replacement of the recipient cell's nucleus with the donor cell's nucleus results in a reconstructed zygote. The ovum may be cultured via ovum transfer, whereby the reconstructed zygote is transferred to a recipient animal, or cultured in vitro and allowed to develop to term.

Another aspect of the present invention provides a method of producing a cloned avian comprising nuclear transfer in combination with ovum transfer. TPLSM and two-photon laser-mediated ablation is used to perform nuclear transfer wherein the donor nucleus may be of normal karyotype or genetically modified. Accordingly, the replacement of the recipient cell's nucleus with the donor cell's nucleus results in a reconstructed zygote. The ovum may be cultured via ovum transfer, wherein the ovum to containing the reconstructed zygote is transferred to a recipient avian or cultured in vitro. Once transferred, the embryo develops inside the recipient hen and travels through the oviduct of the hen where it is encapsulated by natural egg white proteins and a natural egg shell. The egg which contains endogenous yolk and a reconstructed embryo, is laid and can then be incubated and hatched like a normal chick. The resulting chick may be genetically modified. In one embodiment, the genetically modified cloned avian carries a transgene in all or most of its cells. After maturation, the transgenic avian may lay eggs that contain one or more exogenous protein(s). The combination of nuclear transfer and ovum transfer allows for the preparation of a cloned avian. In an alternative embodiment, ex ovo culture may be used instead of ovum transfer to produce the cloned avian. In a preferred embodiment of the instant invention, the avian is a chicken, duck, quail, turkey, pheasant or ostrich.

Another aspect of the present invention provides for a method of producing a transgenic avian by (i) preparing a transgenic avian, carrying a gene encoding an exogenous protein, using nuclear transfer via two-photon visualization and/or ablation, and (ii) allowing the immature transgenic avian to grow to maturity, wherein the exogenous protein is secreted into the oviduct lumen of the mature avian and deposited into eggs laid by the avian. Preferably, the exogenous DNA comprises a stable transgene and the transgenic avians may be bred and propagated. The novel transgenic avians possess the ability to lay eggs that contain one or more desired, exogenous protein(s).

Yet, another aspect of the present invention provides for a method of producing a knock-out or knock-in avian by (i) preparing a knock-out or knock-in avian according to nuclear transfer via two-photon visualization and/or ablation, and (ii) allowing the immature knock-out or knock-in egg-laying animal to grow to maturity. The knock-out avians are able to lay eggs that contain less than all endogenous proteins normally present in the egg. This allows for the elimination of potential undesired substances found in the egg (e.g., allergens) or suppression of a specific agronomic trait. The knock-in sequence may replace all or part of an endogenous gene of the animal by a functional homologous gene or gene segment of another animal.

Cloned non-human cells, cell lines, embryos, and animals, optionally genetically modified, are encompassed by the instant invention. Transgenic, knock-out, and knock-in animals are also provided. In one embodiment, reconstituted avian embryos, particularly chick embryos, prepared by transferring the nucleus of a donor cell into a suitable recipient cell, are provided. The donor cell may be quiescent or non-quiescent.

Intact avian eggs containing protein(s) exogenous to naturally occurring avian eggs are further provided by the present invention.

DETAILED DESCRIPTION OF THE INVENTION a) DEFINITIONS AND GENERAL PARAMETERS

The following definitions are set forth to illustrate and define the meaning and scope of the various terms used to describe the invention herein.

The term "TPLSM" refers to two-photon laser scanning microscopy. TPLSM relies upon the phenomenon of two-photon excited fluorescence in which two photons collide simultaneously with a fluorescent molecule. Their combined energy is absorbed by the fluorophore inducing a fluorescent emission, which is detected by a photomultiplier and converted into a digital image. The major advantage of TPLSM lies in its ability to generate images of living and optically dense structures for prolonged periods of time, while not affecting their viability. This is the case because TPLSM utilizes biologically innocuous pulsed infrared light that is able to penetrate much deeper into scattering specimens. Hence this method provides the capability for producing noninvasive, three-dimensional, real-time images of the optically dense oocyte (e.g., avian egg).

In addition to visualization, TPLSM may also be used for enucleation.

The terms "ovum" and "oocyte" are used interchangeably herein. Although only one ovum matures at a time, an animal is born with a finite number of ova. Ovulation, the shedding of an egg from the ovarian follicle, occurs when the brain's pituitary gland releases a luteinizing hormone, LH. Mature follicles form a stalk or pedicle of connective tissue and smooth muscle. Immediately after ovulation the follicle becomes a thin-walled sac, the post-ovulatory follicle. The mature ovum erupts from its sac and starts its journey through the oviduct. Eventually, the ovum enters the infundibulum where fertilization occurs. Fertilization must take place within 15 minutes of ovulation, before the ovum becomes covered by albumen. During fertilization, sperm (avians have polyspermic fertilization) penetrate the blastodisc, the small white spot on the top side of the yolk where the embryo will develop. When the sperm lodges within this germinal disk, an embryo begins to form. It is now known as a "blastoderm" or "zygote".

A "donor cell" is used herein to describe the source of the nuclear structure that is transplanted to the recipient cytoplast. All cells of normal karyotype, including embryonic, fetal, and adult somatic cells, preferably in a quiescent state, may be nuclear donors. The use of non-quiescent cells as nuclear donors has been described as well by Cibelli, et al. *Science* 280:1256–8, 1998.

A "recipient cell" is used herein to describe the enucleated recipient cell, preferably an enucleated metaphase I or II oocyte, or an enucleated preactivated oocyte. Enucleation may be accomplished by splitting the cell into halves, aspirating the metaphase plate, pronucleus or pronuclei, or even by irradiation. In a preferred embodiment, enucleation is done through two-photon laser-mediated ablation. Alternatively, TPLSM could be used to guide mechanical enucleation.

A "nucleic acid sequence" or "polynucleotide" includes, but is not limited to, eucaryotic mRNA, cDNA, genomic DNA, and synthetic DNA and RNA sequences, comprising the natural nucleotide bases adenine, guanine, cytosine, thymidine, and uracil. The term also encompasses sequences having one or more modified nucleotide(s). The terms "polynucleotide", "oligonucleotide", and "nucleic acid sequence" are used interchangeably herein and include, but are not limited to, coding sequences (polynucleotide(s) or nucleic acid sequence(s) which are transcribed and translated into polypeptide in vitro or in vivo when placed under the control of appropriate regulatory or control sequences); control sequences (e.g., translational start and stop codons, promoter sequences, ribosome binding sites, polyadenylation signals, transcription factor binding sites, transcription termination sequences, upstream and downstream regulatory domains, enhancers, silencers, and the like); and regulatory sequences (DNA sequences to which a transcription factor(s) binds and alters the activity of a gene's promoter either positively (induction) or negatively (repression)). No limitation as to length or to synthetic origin are suggested by the terms described herein.

The terms "endogenous nucleic acid sequence" and "endogenous DNA" are used interchangeably herein. The term "endogenous" as it relates to nucleic acid sequences such as coding sequences, control sequences, and regulatory sequences denotes sequences that are normally associated with a particular cell or tissue. Hence, endogenous sequences are found in nature. Endogenous proteins are the expression products of endogenous DNA, such as endogenous coding sequences.

The terms "exogenous nucleic acid sequence" and "exogenous DNA" are used interchangeably herein. The term "exogenous" as it relates to nucleic acid sequences such as coding sequences, control sequences, and regulatory sequences denotes sequences that are "not" normally associated with a particular cell or tissue. Thus, an "exogenous" region of a nucleic acid is an identifiable segment of nucleic acid within or attached to another nucleic acid molecule that is not found in association with the other molecule in nature. Exogenous DNA may be integrated into the genome of the donor cell or may exist independently of the genome of the donor cell. For example, exogenous DNA may not be integrated into the genome of the donor cell but exist as part of a non-integrated vector in the donor cell.

The term "transgene" refers to exogenous polynucleotide sequence(s) containing a desired coding sequence and control sequences in operable linkage, so that cells transformed with these sequences are capable of producing the encoded product. In order to effect transformation, the transgene may optionally be included on a discrete vector; however, the relevant polynucleotide may also be an integrative vector which has or can become integrated into the host chromosome. A "transgenic animal" is an animal that expresses one or more exogenous gene(s).

The term "knock-out animal" refers to an animal that completely lacks a specific gene that is normally present in its genome.

The term "knock-in animal" refers to an animal that carries a specific nucleic acid sequence such as a "knock-in sequence" in a predetermined coding or noncoding region, wherein the knock-in sequence is introduced through methods of recombination, such as homologous recombination. The recombination event comprises replacing all or part of a gene of the animal by a functional homologous gene or gene segment of another animal, where the respective knock-in sequence is placed in the genomic sequence.

"Vector" means a polynucleotide comprised of single strand, double strand, circular, or supercoiled DNA or RNA, preferably constructed so that a particular coding sequence is located in the vector with the appropriate regulatory sequences, the positioning and orientation of the coding sequence with respect to the control sequences being such that the coding sequence is transcribed under the "control" of the control sequences.

A "plasmid" is a small, circular DNA vector capable of independent replication within a bacterial or yeast host cell.

The terms "transformation", "transduction", and "transfection" all denote the introduction of a polynucleotide into a cell, such as an embryonic or somatic cell.

The term "exogenous protein" means a protein or polypeptide not naturally present in a particular tissue or cell, a protein that is the expression product of an exogenous gene, an exogenous expression construct or a transgene, or a protein not naturally present in a given quantity in a particular tissue or cell.

The term "avian" means a bird of any known species or type. The term includes the various know strains of *Gallus gallus*, or chickens, (for example, White Leghorn, Brown Leghorn, Barred-Rock, Sussex, New Hampshire, Rhode Island, Ausstralorp, Minorca, Amrox, Calif. Gray, Italian Partidge-colored), as well as turkeys, pheasants, quails, duck, ostriches and other poultry commonly bred in commercial quantities.

b) NUCLEAR TRANSFER AND TPLSM

The present invention provides methods for producing cloned animals by nuclear transfer and by combinations of nuclear transfer and embryo transfer. Nuclear transfer allows the cloning of animal species, wherein individual steps are common to the procedures of embryonic, fetal and adult cell cloning. These steps include, but are not limited to, preparation of a chromosome-free recipient cell called a cytoplast (which involves chromosome removal often referred to as enucleation); donor cell nucleus (nuclear donor) isolation and transfer to the cytoplast to produce a reconstructed embryo; optional reconstructed embryo culture; and embryo transfer to a synchronized host animal.

A novel approach to nuclear transfer in animals, employing two-photon visualization, is described in the instant invention. In a preferred embodiment, the fertilized or unfertilized egg is removed from an animal and manipulated in vitro, wherein the genetic material of the egg is visualized and removed and the ablated nucleus replaced with a donor nucleus. Optionally, the donor nucleus may be genetically modified. Two-photon laser scanning microscopy (TPLSM) is used to visualize the nuclear structures. Following visualization, the nucleus in the recipient cell, such as a fertilized or unfertilized egg, is removed or ablated, optionally using TPLSM. TPLSM is based on two-photon excited fluorescence in which two photons collide simultaneously with a fluorescent molecule. Their combined energy is absorbed by the fluorophore, inducing fluorescent emission, which is detected by a photomultiplier tube and converted into a digital image. See Squirrell et al., *Nat. Biotechnol.* 17:763–7, 1999 and Piston et al., *Trends Cell Biol.*, 9:66–9, 1999. TPLSM allows for the generation of images of living, optically dense structures for prolonged periods of time, while not affecting their viability. This is possible because TPLSM utilizes biologically innocuous pulsed near infrared light, usually at a wavelength of about 700 nm to about 1000 nm, which is able to penetrate much deeper into scattering specimens. TPLSM may employ different lasers, such as a mode-locked laser, where the wavelength is fixed, or a tunable laser that can be tuned between about 700 nm and about 1000 nm., depending upon the range of emission of the dye used. For DAPI and Hoescht 33342 dyes, 720–770 nm. is preferred. New fluorophores are being produced with different ranges of emission and the invention is not limited to the presently available dyes and their respective emission ranges.

Furthermore, lasers used in TPLSM can be grouped into femtosecond and picosecond lasers. These lasers are distinguished by their pulse duration. Preferably, a femtosecond laser is used in the instant invention since it is particularly suitable for visualization without harming the specimen.

In a preferred embodiment, TPLSM realizes a method of producing noninvasive, three-dimensional, real-time images of the optically dense avian egg. The ability to visualize the metaphase plate or pronucleus in avian eggs during nuclear transfer has so far been hindered by the presence of the yolk, which makes visualization of these nuclear structures impossible. But two-photon imaging with femtosecond lasers operating in the near infrared allows visualization of nuclear structures without damaging cellular constituents, despite the unfavorable optical properties of the egg yolk. Prior to visualization, specimens may be incubated or injected with DNA-specific dyes such as DAPI (4',6'-diamidino-2-phenylindole hydrochloride) or Hoescht 33342 (bis-benzimide). Prior to incubation, the albumen capsule is removed and the ovum placed in a dish with the germinal disk facing the top. Any remnants of the albumen capsule are removed from the top of the germinal disk. An aqueous solution, e.g. phosphate-buffered saline (PBS), is added to prevent drying of the ovum. A cloning cylinder is placed around the germinal disk and DAPI in PBS is added to the cylinder. Alternatively, a DAPI-PBS solution may be injected into the germinal disk by using a glass pipette, after which the dye moves into the nuclear structures. In the case of injecting the dye, removal of the albumen capsule is not necessary. However, injection of nuclei into the disk is facilitated in the absence of the capsule. Following incubation or injection of DNA-specific dyes, images of the inside of the early avian embryo can be generated through the use of TPLSM. Visualization may be performed after about 10 to 15 minutes of incubation or about 10 minutes after injection. During visualization, the germinal disk is placed under the microscope objective and the pronuclear structures are searched within the central area of the disk using relatively low laser powers of about 3–6 milliwatts. Once the structures are found they may be ablated by using higher laser power or mechanically removed, guided by TPLSM.

Nuclear transfer also requires the destruction or enucleation of the pronucleus before a nuclear donor can be introduced into the oocyte. In order to enucleate the oocyte to produce a cytoplast donor, it is essential to visualize the pronucleus which resides about 25 µm beneath the ovum's vitelline membrane within the germinal disk. Microsurgery has so far been a preferred method to accomplish pronuclear removal or enucleation. However, two-photon laser-mediated ablation of nuclear structures provides an alternative to microsurgery. Higher laser powers than those used for imaging are used for enucleation, with minimal collateral damage to the cell. As during visualization, the wavelength for ablation generally ranges from about 700 nm to 1000 nm, normally about 750 nm. TPLSM and two-photon laser-mediated ablation are more efficient than alternative methods because they are less operator dependent and less invasive, which results in higher viability of the recipient cell. Following visualization, pronuclear structures may be ablated using higher laser powers of about 30 to about 70 milliwatts.

Enucleation is followed by renucleation, where a cultured somatic cell nucleus (nuclear donor) is injected into the enucleated recipient cytoplast. Renucleation may be performed under a microscope on a micromanipulation unit comprising a microinjector and a micromanipulator. Following ablation, the nuclear donor is introduced into the germinal disk though guided injection using episcopic illumination (i.e., light coming through the objective onto the sample). The reconstructed zygote may then be surgically transferred to the oviduct of a recipient hen to produce a hard shell egg. Alternatively, the reconstructed embryo may be cultured for 24 hours and screened for development prior to surgical transfer. The egg can be further incubated to generate a cloned chick, optionally genetically modified. The cloned chick may carry a transgene in all or most of its cells. After maturation, the transgenic avian may lay eggs that contain one or more desired, exogenous protein(s). Alternatively, the resulting chick may be a knock-out animal capable of laying eggs that contain less than all endogenous proteins normally present in the egg. The cloned chick may also be a knock-in chick expressing an alternative phenotype or capable of laying eggs having an exogenous protein therein. The reconstructed egg may also be cultured to term using the ex ovo method described by Perry et al. (supra). In a preferred embodiment of the invention, the animal is an avian including, but not limited to, chickens, ducks, turkeys, quails, pheasants and ostriches.

The replacement of the recipient cell's nucleus with the donor cell's nucleus results in a reconstructed zygote. In a preferred embodiment, the cytoplasmic membrane of the cell used as nuclear donor is disrupted to expose its nucleus to the ooplasm of the recipient cytoplast. The nuclear donor may be injected into the germinal disk, where it undergoes reprogramming and becomes the nucleus of the reconstructed one-cell embryo. Alternatively, a donor cell may be fused to the recipient cell using methods well known in the art, e.g. by means of fusion-promoting chemicals, such as polyethylene glycol, inactivated viruses, such as Sendai virus, or electrical stimulation.

The methodologies of TPLSM and two-photon laser-mediated ablation described herein, can also be used for selective visualization and destruction of specific structures within germ and/or somatic cells including nuclear transfer in mammalian species and other vertebrate species. The skilled artisan will be able to readily adapt the methods established for avians described herein to other types of animals including, but not limited to, mammals, fish, reptile(s), amphibian(s), and insect(s).

c) OVUM TRANSFER

Another aspect of the present invention provides for a method of producing a cloned animal comprising nuclear transfer in combination with ovum transfer. Two-photon visualization and ablation may be used to perform nuclear transfer, as described above. Accordingly, the replacement of the recipient cell's nucleus with the donor cell's nucleus results in a reconstructed zygote. In the preferred embodiment pronuclear stage eggs are used as recipient cytoplasts already activated by fertilization. Alternatively, unactivated metaphase II eggs may serve as recipient cytoplast and activation induced after renucleation. The ovum may be cultured via ovum transfer, wherein the ovum containing the reconstructed zygote is transferred to a recipient hen. The ovum is surgically transferred into the oviduct of the recipient hen shortly after oviposition. This is accomplished according to normal husbandry procedures (oviposition, incubation, and hatching; see Tanaka et al., supra).

In an alternative embodiment, the ovum may be cultured to stage X prior to transfer into a recipient hen. More specifically, reconstructed stage I embryos are cultured for 24–48 hours to stage X. This allows for developmental screening of the reconstructed embryo prior to surgical transfer. Stage I embryos are enclosed within a thick albumen capsule. In this novel procedure, the albumen capsule is removed, after which the nuclear donor is injected into the germinal disk. Subsequently, the capsule and germinal disk are recombined by placing the thick capsule in contact with the germinal disk on top of the yolk. Embryos develop to stage X at similar rates as those cultured with their capsules intact. At stage X, the embryo is transferred to the oviduct of a recipient hen.

Once transferred, the embryo develops inside the recipient hen and travels through the oviduct of the hen where it is encapsulated by natural egg white proteins and a natural egg shell. The egg which contains endogenous yolk and an embryo from another hen, is laid and can then be incubated and hatched like a normal chick. The resulting chick may carry a transgene in all or most of its cells. Following maturation, the cloned avian may express a desired phenotype or may be able to lay eggs that contain one or more desired, exogenous protein(s).

The combination of nuclear transfer and ovum transfer allows for the preparation of a cloned animal that is a complete organism, optionally genetically modified. Genetically modified animals encompassed by the instant invention are transgenics, and knock-in and knock-out animals.

In an alternative embodiment, ex ovo culture may be used instead of ovum transfer to produce the cloned animal (see Perry et al., supra). In a preferred embodiment of the instant invention, the animal is an avian including, but not limited to, chickens, ducks, quails, turkeys, pheasants and ostriches. In another embodiment, the animal is a mammal, fish, reptile, amphibian, or insect.

d) CLONED-, TRANSGENIC-, KNOCK-OUT-, AND KNOCK-IN ANIMALS AND THEIR EGGS

The present invention provides for cloned egg-laying animals produced by nuclear transfer and by combinations of nuclear transfer and ovum transfer as described herein. A novel approach of nuclear transfer, employing two-photon visualization and ablation is used to produce the cloned animals. In addition, the present invention encompasses cloned animals that are genetically modified including, but not limited to, transgenic, knock-out, and knock-in animals.

The instant invention satisfies the need for a rapid route to the expression and deposition of exogenous proteins in eggs. Eggs containing protein(s) exogenous to an egg are also provided by the present invention.

Furthermore, the instant invention provides a novel method of producing cloned, transgenic animals through nuclear transfer via two-photon visualization and ablation, and ovum transfer. Transgenic animals may have their hereditary properties permanently modified by the introduction of recombinant DNA into their germ cells. The combination of zygote reconstruction followed by ovum transfer, as disclosed herein, promises a more efficient and flexible route to accomplish the cloning of animals and production of transgenics. One pertinent use of this technology is the modification of poultry and livestock genomes to improve agronomic traits. Candidate genes, whose introduction or deletion would enhance agronomic traits, can be targeted through use of the instant invention. Most importantly, the possibility of cloning avian species promises tremendous gains for the market place. The new technology disclosed herein may be used in selective poultry breeding, leading to enhanced traits in chickens and their eggs. Further, nuclear transfer techniques developed herein (e.g., laser-mediated selective ablation of nuclear structures of oocytes) also have a wide range of applications in fields such as mammalian transgenesis, genetics, cell therapies, and transplantation.

One aspect of the present invention provides for a method of producing a transgenic animal, comprising the steps of (i) preparing the transgenic animal according to nuclear transfer via two-photon visualization and optionally, laser-mediated ablation, and ovum transfer which contains exogenous DNA in its cells, and (ii) allowing the immature transgenic animal to grow to maturity. In the case of an avian, an exogenous protein is secreted into the oviduct lumen of the mature animal and deposited into eggs laid by the animal. In a preferred embodiment of the instant invention, the exogenous DNA comprises a transgene and the resulting transgenic animals can be bred and propagated. Transgenic avians produced by the instant invention also possess the ability to lay eggs that contain one or more desired, exogenous protein(s).

Transgenes are introduced into the ovum of an animal through nuclear transfer via two-photon visualization and ablation, wherein the nuclear donor contains a desired exogenous DNA sequence in its genome. One of ordinary skill in the art will be able to readily adapt conventional methods to insert the desired transgene into the genome of the nuclear donor prior to injection of the nuclear donor into the recipient cytoplast, or prior to fusion of the nuclear donor cell with the recipient cell. For example, a vector that contains one or more transgene(s) may be delivered into the nuclear donor cell through the use of a delivery vehicle. The transgene is then transferred along with the nuclear donor into the recipient ovum. Following zygote reconstruction, the ovum is transferred into the reproductive tract of a recipient hen. In a preferred embodiment, the ovum is transferred into the infundibulum of the recipient hen. After reconstruction, the embryo containing the transgene develops inside the recipient hen and travels through the oviduct of the hen where it is encapsulated by natural egg white proteins and a natural egg shell. The egg is laid and can be incubated and hatched to produce a transgenic chick. The resulting transgenic chick will carry one or more desired transgene(s) in its germ line. Following maturation, the transgenic avian may lay eggs that contain one or more desired, exogenous protein(s) which can be easily harvested.

In one embodiment of the instant invention, a nuclear donor cell is transfected with a vector construct that contains a transgene. Methods for transfection of somatic cell nuclei are well known in the art and include, by way of example, the use of retroviral vectors, retrotransposons, adenoviruses, adeno-associated viruses, naked DNA, lipid-mediated transfection, electroporation and direct injection into the nucleus. Such techniques, particularly as applied to avians, are disclosed in Bosselman (U.S. Pat. No. 5,162,215), Etches (PCT Publication No. WO99/10505), Hodgson (U.S. Pat. No. 6,027,722), Hughes (U.S. Pat. No. 4,997,763), Ivarie (PCT Publication No. WO99/19472), MacArthur (PCT Publication No. WO97/47739), Perry (U.S. Pat. No. 5,011,780), Petitte (U.S. Pat. Nos. 5,340,740 and 5,656,479), and Simkiss (PCT Publication No. WO90/11355), the disclosures of which are incorporated by reference herein.

Another aspect of the present invention provides for a method of producing a knock-out or knock-in animal, comprising the steps of (i) preparing the knock-out or knock-in animal according to nuclear transfer via two-photon visualization and/or ablation, and (ii) allowing the immature knock-out or knock-in animal to grow to maturity.

In one embodiment of the instant invention, the knock-out animal has been manipulated such that an endogenous gene has been removed from the genome of the donor nucleus. This may be accomplished using described protocols for the production of knock-out mice, including the transformation of the nuclear donors with a targeting vector comprising genomic DNA containing the desired modification, flanked by positive (neomycin resistance gene for instance) and/or negative (herpes simplex virus thymidine kinase) or other applicable selectable marker genes, using a number of described strategies such as the so-called "hit and run" (Hasty, et al., Nature 350:243–6, 1991 and Valancius and Smithies, Mol. Cell Biol. 11: 1402–8, 1991), tag and exchange (Askew, et al., Mol. Cell Biol. 13:4115–24, 1993) and double replacement (Stacey, et al., Mol. Cell Biol. 14:1009–16, 1994).

The resulting knock-out animal can be bred and propagated. Animals produced in this fashion are suitable for research purposes mainly to study the effects of specific drugs on the breeding of poultry and certain agronomic traits. These knock-out animals also possess the ability to lay eggs that contain less than all endogenous proteins normally present in the egg, which allows for the elimination of potential undesired substances found in the egg (e.g., allergens).

In another embodiment of the instant invention, a knock-in animal has been manipulated such that it carries a specific nucleic acid sequence such as a "knock-in sequence" in a predetermined coding or noncoding region of its genome. The knock-in sequence may replace all or part of an endogenous gene of the animal by a functional homologous gene or gene segment of another animal. Knock-in animals can be prepared according to a variation of the standard knock-out method, comprising the introduction of a foreign gene into the targeting vector, in such a way that the introduced gene would be under the control of the regulatory elements that normally control the expression of the endogenous gene (Le Mouellic et al., Proc. Natl. Acad. Sci. USA 87:4712–6, 1990) and (McCreath et al., Nature 405:1066–1069, 2000).

Another embodiment of the invention provides a method of producing a protein derived from cloned, genetically modified egg-laying animals as a result of embryo reconstruction followed by ovum transfer. This method comprises producing a hard-shell egg that contains exogenous protein and then isolating the exogenous protein from the egg. An intact avian egg containing protein exogenous to an avian egg is contemplated by the present invention. The transgenic animals of the instant invention include avians that have a transgene encoding an exogenous protein in their oviducts, wherein the avians secrete into their eggs the protein expressed by the transgene. A transgenic avian that makes a human protein (e.g., human interferon) will recognize this substance as its own and will therefore not produce an immune response against it. This makes the egg-laying transgenic ideally suited for the production of large quantities of human protein. In this respect, the avian egg provides an ideal container for the production of recombinant proteins because its interior is sterile and contains antibacterial compounds, and it is easily accessible. As a consequence, the purity of the protein products can be improved and their efficacy tested more efficiently. Several proteins that may be produced in this fashion are contemplated by the present invention. These proteins include, but are not limited to, human growth hormone, interferon, β-casein, α-1 antitrypsin, antithrombin III, collagen, factor VIII, factor IX, factor X, fibrinogen, hyaluronic acid, insulin, lactoferrin, protein C, erythropoietin (EPO), granulocyte colony-stimulating factor (G-CSF), granulocyte macrophage colony-stimulating factor (GM-CSF), tissue-type plasminogen activator (tPA), feed additive enzymes, somatotropin, and chymotrypsin.

e) EXAMPLES

The following specific Examples are intended to illustrate the invention and should not be construed as limiting the scope of the claims:

Example 1

Preparation of the Recipient Cytoplast

Incubation

Ova were isolated from euthanized hens between 2–4 hours after oviposition of the previous egg. Alternatively, eggs were isolated from hens whose oviducts have been fistulated (Gilbert and Woodgush, Journal of Reproduction and Fertility 5:451–453, 1963) and (Pancer et al. Br. Poult. Sci. 30:953–7, 1989).

Prior to generating images of the avian early embryo, incubation of the DNA specific dye was performed according to the following protocol: The albumen capsule was removed and the ovum placed in a dish with the germinal disk facing the top. Remnants of the albumen capsule were removed from the top of the germinal disk. Phosphate buffered saline was added to the dish to prevent drying of the ovum. A cloning cylinder was placed around the germinal disk and 1.0 µg/ml of DAPI in PBS was added to the cylinder. Visualization was performed after approximately 15 minutes of incubation.

Injection

Preparation of the egg was done as described for incubation. Following removal of the capsule, 10–50 nanoliters of a 0.1 µg/ml solution of DAPI in PBS was injected into the germinal disk using a glass pipette. Visualization was performed approximately 15 minutes after injection.

Visualization

Following incubation, images of the inside of the avian early embryo were generated through the use of TPLSM. The germinal disk was placed under the microscope objective, and the pronuclear structures were searched within the central area of the disk, to a depth of 60 µm using low laser power of 3–6 milliwatts at a wavelength of 750 nm. Once the structures were found they were subsequently ablated.

Nuclear Ablation and Enucleation

Pronuclear structures were subjected to laser-mediated ablation. In these experiments, an Olympus 20×/0.5 NA (Numerical Aperture) water immersion lens was used. The x and y planes to be ablated were defined with the two photon software, while the z plane (depth) was just under 10 µm for this type of objective. Since the pronuclear structure was about 20 µm in diameter, the ablation comprised two steps (2 times 10 µm). The focal point was lowered to visualize the remaining of the pronucleus, which was subsequently ablated. The laser power used to ablate the pronuclei was between 30 to 70 milliwatts at a wavelength of 750 nanometers. For the ablation experiments described above, the image was zoomed by a factor of 4 to 5, giving an area compression of 16–25 fold. Then the power was increased 10–12 fold for a total intensity increase of 160–300 fold compared to the visualization intensity of 3–6 milliwatts. The ablation intensity (power density) is the functional parameter, i.e. the power increase of 10–12 fold results in ablation power of 30–70 milliwatts, but the zoom factor compressed this power into an area 16–25× smaller giving a power density increase of 160–300 fold.

Example 2

Preparation of the Nuclear Donor Cell

Isolation of the Donor Nucleus

Fibroblast cells in cultured were trypsinized (0.25% Trypsin and 1 µM EDTA, Gibco catalog #25200–056), centrifuged twice in PBS containing 5% of Fetal Calf Serum and placed in a 60 mm plastic dish in PBS containing 5% of Fetal Calf Serum. Using the microscope/micromanipulation unit described below, under transmission light, the nuclear donors were then isolated by repeated pipetting of the cells, which disrupted the cytoplasmic membrane and released the nucleus from inside the cell.

Example 3

Preparation of the Reconstructed Zygote

Injection

A micromanipulation unit, comprising a IM-16 microinjector and a MM-188NE micromanipulator, both from Nikon/Marishige, were adapted to an upright Nikon Eclipse E800. This microscope was adapted to operate under both transmission and reflective light conditions. This unique configuration has allowed us to morphologically examine and prepare (isolate the nuclei, as described above) somatic cells in suspension and to load the injection pipette using dry or water immersion lenses under diascopic illumination or transmitted light. This was followed by prompt localization and positioning of the germinal disk under the microscope and subsequent guided injection of the somatic cells, using dry and long distance lenses under fiber optic as well as episcopic illumination (light coming from the side and through the objectives onto the sample respectively).

Example 4

Ovum Transfer

At the time of laying, recipient hens are anesthetized by wing vein injection with pentobarbital (0.7 ml of a 68 mg/ml solution). At this time, the infundibulum is receptive to receiving a donor ovum but has not yet ovulated. We have also established that pentobarbital is the anesthetic of choice. Feathers are removed from the abdominal area, and the area is scrubbed with betadine, and rinsed with 70% ethanol. The bird is placed in a supine position and a surgical drape is placed over the bird with the surgical area exposed. An incision is made beginning at the junction of the sternal rib to the breastbone and running parallel to the breastbone. The length of the incision is approximately two inches. After cutting through the smooth muscle layers and the peritoneum, the infundibulum is located. The infundibulum is externalized and opened using gloved hands and the donor ovum is gently applied to the open infundibulum. The ovum is allowed to move into the infundibulum and into the anterior magnum by gravity feed. The internalized ovum is placed into the body cavity and the incision closed using interlocking stitches both for the smooth muscle layer and the skin. The recipient hen is returned to her cage and allowed to recover with free access to both feed and water. Recovery time for the bird to be up, moving and feeding is usually within 45 min. of the operation's end. Eggs laid by the recipient hens are collected the next day, set, and incubated in a Jamesway incubator. They will hatch 21 days later.

Alternatively, a hen whose oviduct is fistulated allows the collection of eggs for enucleation (Gilbert and Woodgush, *Journal of Reproduction and Fertility* 5:451–453, 1963) and (Pancer, et al. *Br Poult Sci* 30: 953–7, 1989) as mentioned previously, but also the transfer of the reconstructed embryo to a recipient hen for the production of a hard shell egg (Wentworth, *Poultry Science* 39:782–784, 1960). The first technique could be used to obtain ova for recipient cytoplasts and the latter to produce recipient hens to be used repeatedly for the transfer of reconstructed embryos. If they can be made to work, both, and especially the latter technique, should increase the output by reducing the time spent on collection and surgeries.

All documents cited in the above specification are herein incorporated by reference. Various modifications and variations of the present invention will be apparent to those skilled in the art without departing from the scope and spirit of the invention. Although the invention has been described in connection with specific preferred embodiments, it should be understood that the invention as claimed should not be unduly limited to such specific embodiments. Indeed, various modifications of the described modes for carrying out the invention which are obvious to those skilled in the art are intended to be within the scope of the following claims.

What is claimed is:

1. A method of enucleating an avian oocyte comprising: visualizing internal structure of an avian oocyte utilizing two-photon laser scanning microscopy (TPLSM) and ablating the nucleus of the oocyte by near-infrared light, thereby enucleating the avian oocyte.

2. The method of claim 1 wherein the oocyte is injected or incubated with a DNA specific dye.

3. The method of claim 2 wherein the dye is DAPI or Hoescht 33342.

4. The method of claim 1 wherein the oocyte is a chicken oocyte.

5. The method of claim 1 wherein the oocyte is at metaphase I.

6. The method of claim 1 wherein the oocyte is at metaphase II.

7. The method of claim 1 wherein the oocyte is a germinal disc.

8. The method of claim 1 wherein the TPLSM employs a femtosecond laser.

9. The method of claim 1 wherein the near-infrared light has a wavelength in a range of about 700 nm to about 1000 nm.

10. The method of claim 1 wherein the near-infrared light has a wavelength of 750 nm.

11. The method of claim 1 wherein the visualizing is done using a laser power of about 3 to about 6 milliwatts.

12. The method of claim 1 wherein the nucleus is ablated using laser power of about 30 milliwatts to about 70 milliwatts.

13. A method of enucleating an avian zygote comprising:
visualizing internal structure of an avian pronuclear zygote utilizing two-photon laser scanning microscopy (TPLSM) and ablating the nucleus of the pronuclear zygote, thereby enucleating the avian zygote.

14. The method of claim 13 wherein the zygote is injected or incubated with a DNA specific dye.

15. The method of claim 14 wherein the dye is DAPI or Hoescht 33342.

16. The method of claim 13 wherein the zygote is a chicken zygote.

17. The method of claim 13 wherein the zygote is a pronuclear zygote.

18. The method of claim 13 wherein the TPLSM employs a femtosecond laser.

19. The method of claim 13 wherein the near-infrared light has a wavelength in a range of about 700 nm to about 1000 nm.

20. The method of claim 13 wherein the near-infrared light has a wavelength of 750 nm.

21. The method of claim 13 wherein the visualizing is done using a laser power of about 3 to about 6 milliwatts.

22. The method of claim 13 wherein the nucleus is ablated using laser power of about 30 milliwatts to about 70 milliwatts.

23. A method of enucleating an avian oocyte or avian zygote comprising:
visualizing internal structure of an avian oocyte or avian zygote utilizing two-photon laser scanning microscopy (TPLSM) at a laser power of about 3 milliwatts to about 6 milliwatts and ablating the nucleus of the oocyte or zygote by infrared light, thereby enucleating the avian oocyte or avian zygote.

24. The method of claim 23 wherein the oocyte or zygote is a chicken oocyte or zygote.

25. The method of claim 23 wherein the near-infrared light has a wavelength in a range of about 700 nm to about 1000 nm.

26. The method of claim 23 wherein the nucleus is ablated using laser power of about 30 milliwatts to about 70 milliwatts.

27. A method of enucleating an avian oocyte or avian zygote comprising:
visualizing the internal structure of an avian oocyte or avian pronuclear zygote utilizing two-photon laser scanning microscopy (TPLSM) and ablating the nucleus of the oocyte or zygote by near-infrared light having a wavelength of about 700 nm to about 1000 nm, thereby enucleating the avian oocyte or avian zygote.

28. The method of claim 27 wherein the oocyte or zygote is a chicken oocyte or zygote.

29. The method of claim 27 wherein the near-infrared light has a wavelength of 750 nm.

30. The method of claim 27 wherein the nucleus is ablated using laser power of about 30 milliwatts to about 70 milliwatts.

31. A method of enucleating an avian oocyte or avian zygote comprising:
visualizing internal structure of an avian oocyte or avian zygote utilizing two-photon laser scanning microscopy (TPLSM) and ablating the nucleus of the oocyte or pronuclear zygote by near-infrared light using a laser power of about 30 milliwatts to about 70 milliwatts, thereby enucleating the avian oocyte or avian zygote.

32. The method of claim 31 wherein the oocyte or zygote is a chicken oocyte or zygote.

33. The method of claim 31 wherein the near-infrared light has a wavelength in a range of about 700 nm to about 1000 nm.

* * * * *